(12) United States Patent
Deemer et al.

(10) Patent No.: US 8,476,075 B2
(45) Date of Patent: Jul. 2, 2013

(54) ANALYTICAL TECHNIQUE FOR MEASURING BOUND GLYCERIDES IN A BIODIESEL COMPOSITION

(75) Inventors: Eva Deemer, El Paso, TX (US); Wen Yee Lee, El Paso, TX (US); Xiomara Carolina Chianelli, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 101 days.

(21) Appl. No.: 12/755,126

(22) Filed: Apr. 6, 2010

(65) Prior Publication Data

US 2010/0261281 A1 Oct. 14, 2010

Related U.S. Application Data

(60) Provisional application No. 61/166,831, filed on Apr. 6, 2009.

(51) Int. Cl.
*G01N 33/22* (2006.01)
*G01N 30/90* (2006.01)

(52) U.S. Cl.
USPC ........... 436/71; 436/60; 436/128; 436/131; 436/139; 436/162; 436/164; 436/172; 436/174; 436/800; 422/69; 422/70; 422/82.08; 73/61.54; 73/61.55; 73/61.59; 73/64.56; 210/658

(58) Field of Classification Search
USPC ............ 436/60, 71, 128, 131, 132, 139, 161, 436/162, 164, 169, 172, 174, 177, 178, 800; 422/420, 69, 70, 82.05, 82.08; 73/61.52, 73/61.54, 61.55, 61.59, 64.56; 210/656, 658; 702/25
See application file for complete search history.

(56) References Cited

U.S. PATENT DOCUMENTS

| 4,259,440 A | 3/1981 | Gupta et al. | |
|---|---|---|---|
| 2005/0227369 A1* | 10/2005 | Richardson et al. | 436/169 |
| 2006/0213554 A1* | 9/2006 | Welch et al. | 137/93 |

FOREIGN PATENT DOCUMENTS

CN 101290308 10/2008

OTHER PUBLICATIONS

Fowler et al. Journal of Lipid Research, vol. 28, 1987, pp. 1225-1232.*
Bansal et al. Fuel, vol. 87, Jun. 2, 2008, pp. 3369-3372.*
Eva et al. Preprints of Symposia-Americal Chemical Society, Division of Fuel Chemistry, vol. 53(1), 2008, pp. 404-405.*
Eva et al. Preprints of Symposia-American Chemical Society, Division of Fuel Chemistry, vol. 54(1), 2009, pp. 18-19.*
Akgun, et al., "Effects of Process Variables for Biodiesel Production by Tranesterification," Eur. J. Lipids Sci. Technology (2007) 109:486-492.
Alleman, et al., "2006 B100 Quality Survey Results: Milestone Report," NREL/TP-540-41549 May 2007, 36 pages.
Bondioli, et al., "An Alternative Spectrophotometric Method for the Determination of Free Glycerol in Biodiesel," Eur. J. Lipid Sci. Technol. (2005) 107:153-157.
Fowler, et al., "Use of nile red for the rapid in situ quantitation of lipids on thin-layer chromatograms," Journal of Lipid Research (1987) 28:1225-1232.
Freedman, et al., "Transesterification kinetics of soybean oil," JAOCS (1986) 63(10), pp. 1375-1380.
Greenspan, et al., "Nile red: a selective fluorescent stain for intracellular lipid droplets," J Cell Biol. (1985) 100:965-973.
Heiden, Richard W., "Analytical Methodolofies for the Determination of Biodiesel Ester Purity—Determination of Total Methyl Esters," Final Report, Feb. 27, 1996, 48 pages.
Knothe, G., "Analyzing Biodiesel: Standards and other Methods," JAOCS (2006) 82(10):823-833.
Lotero, et al., "Synthesis of Biodiesel via Acid Catalysis," J Ind Eng Chem Res (2005) 44:5353-5363.
Lozano, P., et al., "Measurement of Free Glycerol in Biofuels," Fresenius J. Anal. Chem., (1996), 354:319-322.
Plank, et al., "Simultaneous Determination of Glycerol, and Mono-, Di-, and Triglycerides in Vegetable Oil Methyl Esters by Capillary Gas Chromatography," J. Chromatogr. A. (1995) 697:461-468.
Rashid, et al., "Production of Biodiesel through Optimized Alkaline-Catalyzed Transesterification of Rapeseed Oil," Fuel (2008) 87:265-273.
Orata, Frances, "Derivatization Reactions and Reagents for Gas Chromatography Analysis, Advanced Gas Chromatography," InTech, Mar. 2012, pp. 83-108.
Pierce, "GC Derivatization," Applications Handbook & Catalog, 2003-2004, pp. 1-5.
Sigma-Aldrich, "Guide to Derivatization Reagents for GC," Bulleton 909A, 1997.
Schummer, Claude, et al., "Comparison of MTBSTFA and BSTFA in derivatization reactions of polar compounds prior to GC/MA analysis," Talanta, 77 (2009), 1473-1482.

* cited by examiner

*Primary Examiner* — Maureen Wallenhorst
(74) *Attorney, Agent, or Firm* — Edwin S. Flores; Chainey P. Singleton; Chalker Flores, LLP (57) ABSTRACT

A method of estimating the amount of unreacted starting materials (glycerides, methyl esters, etc.) and the composition of a biodiesel using TLC in conjunction with a lipophilic dye, Nile Red is described herein. The dye based TLC method of the present invention is convenient and provides significant advantages over existing methods for estimating the purity of a biodiesel composition.

19 Claims, 2 Drawing Sheets

FIG. 1

Overall Reaction:

Stepwise Reactions:

ANALYTICAL TECHNIQUE FOR MEASURING BOUND GLYCERIDES IN A BIODIESEL COMPOSITION

CROSS-REFERENCE TO RELATED APPLICATIONS

This application claims priority to U.S. Provisional Application Ser. No. 61/166,831, filed Apr. 6, 2009, the entire contents of which is incorporated herein by reference.

TECHNICAL FIELD OF THE INVENTION

The present invention relates in general to the field of estimating the purity of a biodiesel composition, and more particularly, to the development of a dye based analytical technique for determining the amount of bound glycerides and unreacted starting materials in a biodiesel composition.

STATEMENT OF FEDERALLY FUNDED RESEARCH

None.

BACKGROUND OF THE INVENTION

Without limiting the scope of the invention, its background is described in connection with the development of a dye based analytical technique for the determination of contaminants (unreacted starting materials) in a biodiesel composition and for the assessment of the overall conversion of the transesterification reaction for the production of a biodiesel.

US Patent Publication No. 20060213554 (Welch et al. 2006)[1] describes a process and system for the analysis and/or control of a mixture of liquid hydrocarbons and biodiesel to determine biodiesel concentration includes measuring the near infrared absorption in at least two of the bands of two absorption bands from a portion of the range of 800-2500 nm; in particular 1100-2500 nm which are used to quantify the biodiesel content.

Publication No. CN 101290308 (Zhu et al. 2008)[2] discloses a method for compartment analysis of a glyceride composition through high performance liquid chromatography involving a step of pretreatment, during which, the ferulic acids and absolute ethyl alcohols generate reflux heating reaction under the catalysis of thionyl chlorides and are dissolved in an ether and then ferulic acid methyl ethyl oxalate is obtained after extraction through sodium bicarbonate; under the temperature of between 30 and 50 DEG C., the ferulic acid glycerol monobutyralte is dissolved in methanol, filtered and then diluted by HPLC-level methanol followed by HPLC analysis.

U.S. Pat. No. 4,259,440 (Gupta and Chaudhari, 1981)[3] disclose a method and a composition for the hydrolysis and assay of triglycerides. The method includes the steps of adding lipase and cholesterol esterase to a triglyceride in combination with a glycerol assay system and determining the amount of triglycerides present based on the amount of glycerol produced. The composition includes a mixture of lipase, cholesterol esterase and a glycerol assay system.

SUMMARY OF THE INVENTION

The present invention discloses an analytical method using lipophilic dyes, e.g., Nile Red, for determining the amount of bound glycerides and unreacted starting materials in a biodiesel composition. The method of the present invention can also be used for calculating the conversion rate of a transesterification reaction for the formation of a biodiesel and for the assessment of the composition and the purity of a biodiesel composition.

In one embodiment the present invention describes a thin-layer chromatography (TLC) method for detecting the amounts of one or more suspected contaminants in a fuel sample using a fluorescent lipophilic dye. The steps involved include: (i) obtaining the fuel sample, (ii) separating the fuel sample along with a standard sample of the suspected contaminants on one or more coated TLC plates, (iii) submerging the TLC plate in a solution comprising the fluorescent lipophilic dye to stain the plates, (iv) drying the stained plates, (v) dipping the dried and stained plates in a bleach solution, (vi) visualizing the one or more bands on the coated plate using an UV lamp, and (vii) determining the amounts of the one or more suspected contaminants by comparing a region of interest for the standard and the fuel sample.

The method as described herein above further comprises the steps of capturing one or more images, validating the accuracy of the standard using a mass curve, plotting a graph to calculate a $R^2$ value for each plate, and calculating of one or more masses for the one or more suspected contaminants in the sample. The one or more calculated masses for the one or more suspected contaminants is then directly correlated with an overall conversion rate of a chemical reaction and with the overall composition and purity of a sample.

In one aspect of the present invention the fuel sample is selected from one or more renewable fuels, biofuels, biodiesel, vegetable oils, alkyl esters, and ethanol and the suspected contaminants comprise of one or more lipids, glycerides, esters, fatty acids, glycerol, methyl esters or any combinations thereof. In another aspect the fuel sample and the standards are deposited directly or deposited after dissolution in an organic liquid. In yet another aspect the coated plate is selected from glass, plastic, aluminum or aluminum foil, comprising a coating selected from silica gel, aluminum oxide, cellulose or any other adsorbent material. The solvent or solvent mixture comprises hexane, diethyl ether, acetic acid, organic solvents or any combinations or mixtures thereof. In a further aspect the dye solution comprises one or more lipophilic dyes selected from Nile Red, Oil-Red-O, Sudan Black B, or other lipophilic stains and the coated plate is submerged in a solution of a lipophilic dye until the coated plate is stained. The dried plate is placed in a bleach solution selected from sodium hypochlorite, hydrogen peroxide, sodium perborate, sodium percarbonate, sodium persulfate, sodium perphosphate or calcium hypochlorite. In a certain aspect the analytical method using the lipophilic fluorescent dye can be used to assess the completion of a chemical reaction, wherein the reaction is a transesterification reaction.

In another embodiment the present invention provides an analytical method for detecting the amounts of one or more suspected contaminants in a fuel sample using a fluorescent lipophilic dye comprising the steps of: obtaining the fuel sample and depositing the fuel sample and a standard of the one or more suspected contaminants onto the coated plate. This is followed by placing the coated plate in a solvent or a solvent mixture. After a specified amount of time the coated plate is removed from the solvent or a solvent mixture and dried. The dried coated plate is submerged in a solution comprising a fluorescent lipophilic dye. After removing the coated plate from the fluorescent lipophilic dye solution it is dried and dipped in a bleach solution. After drying, the one or more bands on the coated plate are visualized using an UV lamp and the amounts of one or more suspected contaminants by are determined by comparing a region of interest for the standard and the fuel sample.

In yet another embodiment, the present invention teaches an analytical method for detecting the amounts of one or more suspected contaminants in a biodiesel sample using a lipophilic fluorescent dye comprising the steps of: (i) obtaining a biodiesel sample, (ii) depositing the biodiesel sample and a standard of the one or more suspected contaminants onto a coated plate, wherein the biodiesel sample is deposited directly or deposited after dissolution in an organic liquid, (iii) placing the coated plate in a solvent or a solvent mixture for a specified amount of time, (iv) removing the coated plate from the solvent or a solvent mixture followed by drying, (v) submerging the dried coated plate in a solution of the fluorescent lipophilic until stained, (vi) removing the coated plate from the dye solution, drying the coated plate and dipping the dried coated plate in a bleach solution followed by a second drying step, (vii) visualizing the one or more bands on the coated plate using an UV lamp, and (viii) determining the amounts of one or more suspected contaminants by comparing a region of interest for the standard and the biodiesel sample.

The analytical method of the present invention further comprises the steps of: capturing one or more images; validation of the accuracy of the standard using a mass curve; plotting a graph to calculate a $R^2$ value for each plate; and calculating one or more masses for the one or more suspected contaminants in the biodiesel sample. The one or more calculated masses for the one or more suspected contaminants are directly correlated with an overall conversion rate of the transesterification reaction for the biodiesel formation.

One aspect of the present invention is directed towards the detection of the suspected contaminants comprising of one or more lipids, glycerides, esters, fatty acids, glycerol, methyl esters or any combinations thereof. In yet another aspect of the present invention the dye solution comprises one or more lipophilic dyes selected from Nile Red, Oil-Red-O, Sudan Black B or other lipophilic stains.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "thin-layer chromatography" (TLC), refers to one of the most standard laboratory techniques. TLC is a solid-liquid partitioning technique used in chemical analysis. It is a micro-scale technique since only micrograms of material are needed to perform the analysis. A thin layer chromatography plate consists of a thin layer of adsorbent material (stationary phase) coated on a backing support. Typically, the support is, but is not limited to, a glass plate and the adsorbent material is, but is not limited to, a silica/silicate material. When the thin layer plate is partially submerged in a liquid (mobile phase), the liquid ascends the adsorbent by capillary action. By placing a small spot of a solution containing two compounds near the base of the thin layer plate, yet not immersed in the solvent, the ascending liquid carries the sample and partitions the sample between the adsorbent stationary phase and the liquid mobile phase (commonly referred to as developing). After development, the plate can be visualized and the distance a given compound travels with respect to the distance the solvent travels is referred to as the compound's Rf value and is expressed as a ratio. Different compounds have different interactions with the prescribed mobile and stationary phases and have a unique Rf of their own. Hence, thin layer chromatography is useful in determining the number of compounds in a given mixture. If the compounds in the mixture have very different chemical structures and the mobile/stationary phases are chosen properly, upon elution (development) the compounds will separate into their own spots with visible Rf differences between the spots.

The term "gas chromatography" (GC) is used to describe the process of separating and redistributing molecules in a mixture from a thin material phase to a second bulk material phase comprising a gas stream. The gas stream is then analyzed to obtain information specific to the transfer molecules. Typical detection systems include thermal conductivity, flame ionization, and argon detectors.

The term "high performance liquid chromatography" (HPLC), as used herein, refers to the separation of molecules under high pressure (around 500-3500 psi) in a column filled with a matrix (between 3 and 50 microns). Molecules are separated according to their physical properties such as their size, shape, charge, hydrophobicity, and affinity for other molecules. In general, the components to be separated are distributed between two phases: a stationary phase bed and a mobile phase which percolates through the stationary bed. A mixture of various components enters a chromatography process, and the different components are flushed through the system at different rates. These differential rates of migration as the mixture moves over adsorptive materials provide separation. Repeated sorption/desorption acts that take place during the movement of the sample over the stationary bed determine the rates. The smaller the affinity a molecule has for the stationary phase, the shorter the time spent in a column.

The term "lipid" refers to any one or more of a group of substances that in general are soluble in ether, chloroform, or other solvents for fats but are only sparingly soluble in water, that with proteins and carbohydrates constitute the principal structural components of cells, and that are considered to include fats, waxes, phosphatides, cerebrosides, and related and derived compounds and may even include steroids and carotenoids. The term "glycerides" as used herein is intended to include compositions having a major portion of monoglycerides, preferably at least 60% by weight and most preferably about 90% by weight. Also, the glyceride compositions may include some diglyceride, preferably no more than about 40% by weight and most preferably no more than about 10% by weight. The glyceride compositions may also include some triglycerides, preferably no more than about 10% by weight.

The term "contaminant" refers to a minor and an unwanted constituent in another material, metal, chemical or mixture, often at the trace level. In chemistry, the term usually describes a single chemical, but in specialized fields the term can also mean chemical mixtures, even up to the level of cellular materials.

As used herein the term "esterification" or "transesterification" are the processes by which an acid group is added, hydrolyzed, repositioned or replaced on one or more components of the substrate. The acid group can be derived from a fat or oil which is part of the initial substrate or from a free fatty acid or ester that has been added to the deodorized substrate or purification media-processed substrate. The term "transesterification" includes the process in which R, R' or R" on a glyceride is a first fatty acid group given by —OC(=O)R'", and the first fatty acid group is replaced by a second, different fatty acid group. The second fatty acid group which replaces the first fatty acid group can come from the same or different fat or oil present in the initial substrate. The second fatty acid can also come from a free fatty acid or ester added to the deodorized substrate or the purification media-processed substrate.

The term "fuel" as used herein is any material that is burned or altered to obtain energy and to heat or to move objects. Fuel releases its energy either through a chemical reaction means, such as combustion, or nuclear means, such as nuclear fission or nuclear fusion. An important property of a useful fuel is that its energy can be stored to be released only when needed, and that the release is controlled in such a way that the energy can be harnessed to produce work, for example: Methane, Petrol, Wood and Oil.

The term "biodiesel" used in this specification includes mono alkyl esters of a long chain fatty acid derived from renewable lipid sources. Suitable sources include animal fats and vegetable oils, including, for example, soybean oil, sunflower oil, linseed oil, coconut oil, and the like. Other useful biodiesel materials for use in the present invention comprise a mixture of fatty acid esters. Typically these materials are made by the transesterification of vegetable oil to biodiesel. One route to biodiesel involves reacting a vegetable oil (a triglyceride) with an alcohol, preferably methanol, to form biodiesel and glycerol. Biodiesels can comprise methyl esters that contain, for example, $C_6$-$C_{14}$ fatty acids such as caproic, caprylic, capric, lauric, and myristic. The term "biodiesel" can also include, for example, methyl esters of $C_{12}$-$C_{22}$ fatty acids such as lauric acid, myristic acid, palmitic acid, palmitoleic acid, stearic acid, oleic acid, elaidic acid, petroselic acid, ricinoleic acid, elaeosteric acid, linoleic acid, linolenic acid, arachic acid, gadoleic acid, behenic acid, and erucic acid. It should be understood however, that, in other embodiments, other useful biodiesel materials and mixtures of these and other biodiesels, are within the contemplated scope of the present invention.

Glycerides are usually prepared by conventional methods of glycerolysis of edible fats and oils; that is, by reacting glycerine with a fatty acid, glyceride, or other fatty acid ester or by directly esterifying glycerine with a fatty acid having from about 8 to about 22 carbon atoms. Typical of such glycerides are glyceryl monooleate, glyceryl monostearate, and glyceryl monopalmitate.

The present invention discloses the development of a dye based analytical technique for the determination of contaminants (unreacted starting materials) in a biodiesel composition and for the assessment of the overall conversion of the transesterification reaction for the production of a biodiesel.

Biodiesel is an attractive alternative for petrol diesel in the renewable market owing to its technical feasibility and chemical economy. Biodiesel offers many advantages over traditional petroleum diesel in that it is made from renewable resources (biomass), is biodegradable, is nontoxic, contains no sulfur and can be used with little or no modifications required on diesel engines.

Figure 1:
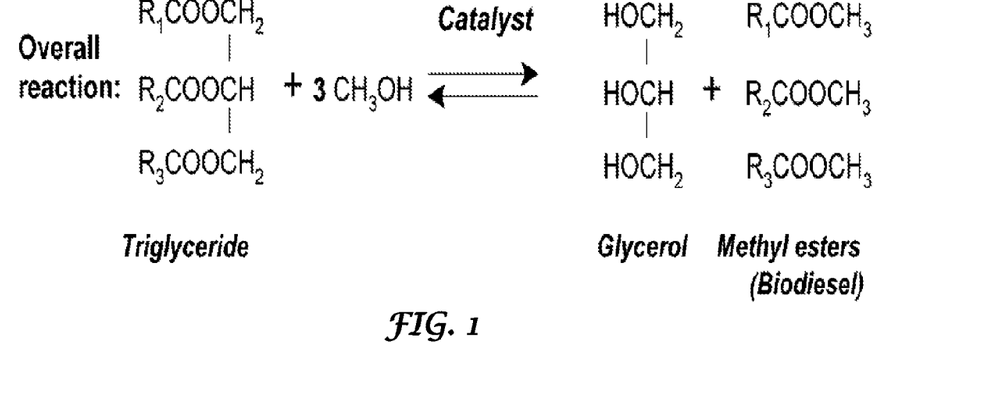
FIG. 1 shows a transesterification reaction[4]

Using animal fats or vegetable oils, it is possible to use a transesterification or esterification reaction to produce mono alkyl-esters. The heavy oil is broken into $C_{18}$-$C_{22}$ carbon chains using a catalyst and methanol. The chemical reactions involved in this process are shown in FIG. 1. As this process is a stepwise reaction, products of incomplete transesterification which include bonded or bound glycerin typically remain as fuel contaminants.

The high level of bonded glycerides causes an increase in crystallization and viscosity[6] and hence is the main concern while in process because it dictates the quality of the conversion which then results in the quality of the fuel. Standards placed by American Standards Testing Material (ASTM) D6751 and European Standard (EN) 14214 precaution anything with higher than 0.24% total glycerol to ensure fuel standardization. A study using Thin Layer Chromatography Flame Ionized Detection (TLC/FID) to correlate Gas Chromatography (GC) determination of conversion to biodiesel found that any conversion >96% had less than 0.25% bonded glycerol. It was never determined however what accounted for the difference in percentages. While the most common detection is the Gas Chromatography Flame Ionized Detection (GC-FID), there is much scientific literature exploring alternative quantitative methods.

Determining the purity of the methyl esters serves the purpose of not only determining the quality of the biodiesel, it is also an in process tool used to adjust quantities which have been undergoing unsatisfactory conversion rates. In an industrial context, there is the matter of accuracy and then there is a separate matter of rapid determination for in process purposes. A preliminary report to the National Biodiesel Board[7] investigating the implementation of GC-FID for ASTM D6751 testing, the accuracy and repeatability of results was described as being limited by a host of variables which need to be carefully controlled. These variables included the calibration process, purity of standards, the inability to quantify all the esters in a sample, the complexity of the samples themselves, peak overlaps and misidentification. It was conclusive that research was needed to improve the quality of methyl ester determinations with reduced effort and complexity. Prospective analytical methods were addressed in the context of the most economical way to obtain the best repeatability and highest accuracy. The immediate implementation of a modified American Oil Chemist Society (AOCS) GC-FID method was introduced to remedy the short term need for a more reliable method to the fore mentioned.

A study report conduced by the National Renewable Energy Lab (NREL) sought to discuss the actualities and feasibility of standardization and quality control. The report was sponsored by the U.S. Department of Energy as efforts of the fuels technologies program multiyear program plan has goals of displacing 5% of diesel derived from fossil fuel with renewable. Samples within the United States met a failure rate of 59%. The highest single failure rate was observed for free and bound glycerin or total glycerin.[8]

Figure 2:
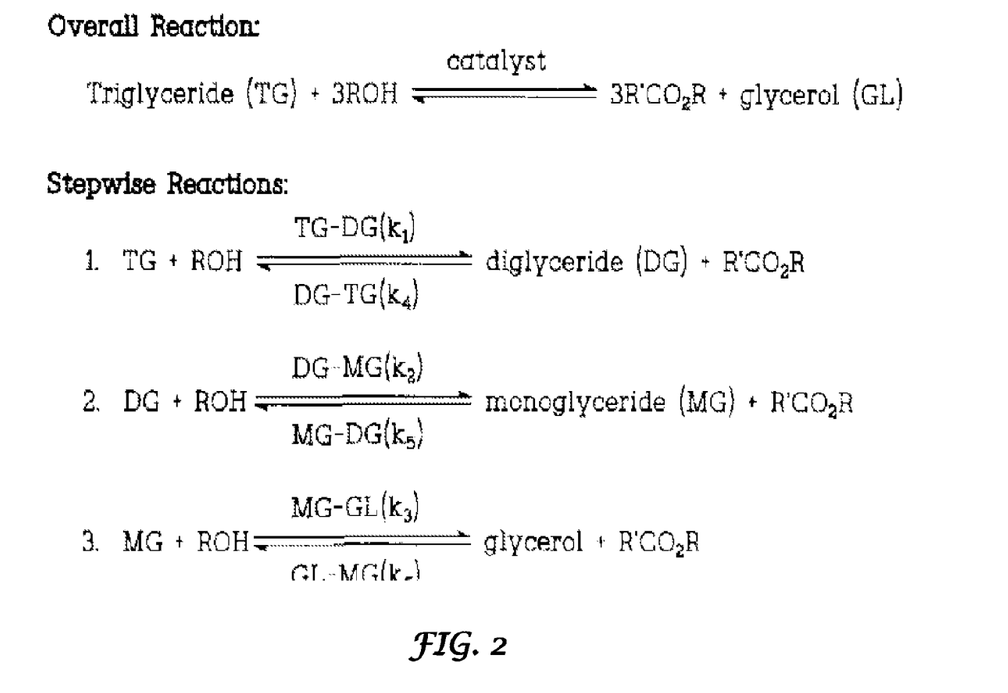
FIG. 2 shows the stepwise conversion of triglyceride to biodiesel[5]

The amount of glycerides remaining demonstrates the degree of conversion (FIG. 2). High levels of glyceride can cause problems with engine components such as the fuel injector. Bound glycerides are not very soluble in biodiesel and contribute to higher melting points and engine coking In the presence of moisture, monoglycerides crystallize and settle out causing build up. European standards take more notice of individual classes of bound glycerides because of this problem, while ASTM standards only require the total bound glycerin content. Monoglycerides contribute to the high cloud point and have been since the subject of research which has supported the cold soak filtration, the most recent test added to ASTM D6751. This test requires 300 ml of biodiesel to pass through a 0.7 micron glass fiber filter after leaving it at 40° C. for 16 hours. This is carried out under a vacuum and if not completed in 360 seconds it fails. This is the most recent test annexed to the ASTM D6751 but requirements for monoglycerides are already specified in EN methods as this impurity poses a serious threat in cold temperatures.

Gas Chromatography: For the studies conducted in the present invention reagent grade standards and reagents were purchased. Standard solutions were made up as a five level calibration containing the compounds of interest: glycerin, monoolien, diolien, and triolien. These compounds were purchased in pyridine and then diluted with heptanes. Calibration was carried out under the same conditions as sample analysis. 1 µl is injected into the GC and a chromatogram and peak integration report was created using response factors generated by the calibration. This process took three hours since it was a five level calibration and each run was 45 minutes long.

In this method, it was necessary to silyate molecules to lower volatility or to a higher molecular weight like bonded glycerol components.[6] This derivatization added trimethylsilyl across the hydroxyl (—OH) groups present in the molecule; if the molecule had no hydroxyl group such as triglyceride or mono alkyl esters (biodiesel) then it remained unaffected. MSTFA has been implemented in the official ASTM method because of its high reactivity. However, it is also highly reactive with water and forms disiloxane in the presence of air containing any moisture, which renders it useless for the reaction and to detect glycerides. This methodology was justified by the recovery of internal standards (2,3,4 butantriol and tricaprin)[9] and a five level calibration using the compounds of most interest: glycerol, monoolein, diolein, and triolein.

Problems surrounding the repeatability predispose the industry to continue improving current methods but little progress has been made in instituting an easier, accurate and more suitable determination of methyl ester purity.

In all cases of comparison between methods and instrumentation, the scientific understanding of analytical performance is determined through empirical information. The 'Christina Plank' method[10] is currently the ASTM D6584 requirement which improved upon internal standards and the use of MSTFA as a silyation agent. What was concluded in that highly cited paper, is that the repeatability of prepared standards indicated that the method was suitable for quality control of biodiesel. As adopted by ASTM, this method was 45 minutes long, very specific to the column used and the temperature the samples were run at. While it is assumed that it employs full automation, most often it does not because the automation is more expensive and adds additional time to the analysis. A year after the Christina Plank method was published; it was acknowledged that errors in preparation and standard handling pose a serious threat to repeatability in the context of industry.

Thin Layer Chromatography (TLC): TLC coupled with flame ionization is cited as having standard error a tenth of a percent which is too high for the sensitivity required by commercial biodiesel standards.

High Performance Liquid Chromatography (HPLC): HPLC is a method strongly recommended[5] to void problems due to complexity of samples and to decrease the analysis time therefore allowing for more statistical determination as more samples can be analyzed in less time. It would potentially simplify the calibration with a universal calibration. Rather than separate the lipid impurities into individual compounds and determine each entity, the emphasis of much work is directed at separation of lipids into classes of compounds, such using evaporative light scattering. HPLC detection approaches differ from that of GC where compounds are separated and determined individually. The esters as a group of substances are separated from the various glyceride compounds.

Glycerol: Over the years methods to determine free and bound glycerin have been modified in efforts to determine classes of bound glycerides with more accuracy. It has been suggested however that the total glycerin content can be simply analyzed by converting bound glycerin to free glycerol. While current methods employ the use of the GC, other methods utilizing enzymatic conversion of bound glycerides to free glycerol have been commercially available from Sigma Aldrich. The Greenhill method uses an enzyme to provide an analysis in terms of total glycerol. It was imperative for above method to avoid using the GC which could re-introduce error initially discussed as inherent to the instrumentation itself.

UV Detection: Bondoli et al.[11] have been able to use a spectrophotometric method to determine free glycerol. A periodate oxidation of glycerol to create formaldehyde which reacts further with acetylacetone to form 3,5-diacetyl-1,4-dihydrolutidine. This reaction, called Hantzsch's reaction has a high absorbance at 410 nm and is shown to be capable of low detection limits.

The present invention uses the dye Nile Red for the determination of contaminants (unreacted starting materials) in a biodiesel composition and for the assessment of the overall conversion of the transesterification reaction for the production of a biodiesel. Nile Red is known to be a sensitive stain used for the detection of lipids. It has been used as an intracellular stain technique to visually identify lipid regions for various organisms.[12] As a hydrophobic probe, it is far superior to other fluorescent dyes, which fade rapidly. Rhodamine has been commonly used but hydrogenation of samples is required to saturate fatty acids if an analysis is to be made using TLC. Nile Red is intensely fluorescent, very selective to lipids, photostable and combined with TLC can measured for the quantification of lipid mass.[13]

GC analysis: Standard testing methods for determination of free and total glycerin in B-100 biodiesel outlined in D6584 were carried out independently by two different testing facilities. Sample preparation: 100 mg of sample was dissolved with 100 µl of hexane and placed in a 2 ml vial, and 10 mg of TLC mixture (18-4A) was dissolved in 100 µl of hexane and placed in a 2 ml vial.

TLC: Silica-gel plates were cut into 10 cm×10 cm squares and 0.3 µl of sample was deposited 5 times onto each plate using 0.1 µl pipette to keep size and shape of ROI from distortion. Calibration was introduced a total of 5 times using 0.1 µl pipette to deposit 0.1 µl-0.5 µl on each plate. Each spot was distributed 1 cm apart. Plates were developed in solution (60:30:1 hexane/diethylether/acetic acid) and allowed to dry completely.

Nile Red: Plates were completely dried before staining with nile red in order to keep prevent any loss of sample. Once completely dried, the plates were submerged completely in a nile red solution (8 mg/L, 80:20 methanol-distilled water). Dried plates were then dipped quickly in a dilute bleach solution (1/2500 Clorox-distilled water). Once the plates were completely dried, lipid bands were visualized using UV lamp.[11]

Scanning: Plates were scanned via epi-luminescence at 530 nm-600 nm using a Kodak Molecular Image scanner. ROI's can be manually selected from images. Standards were defined by selecting ROI's in a standards list and entering name and mass. The spot with the highest fluorescence (final triglyceride of the calibration) was selected as a reference. Once assigned, standards can be validated for accuracy using a mass curve. $R^2$ values are obtained and the quality of each plate can be verified before samples are read. Entered mass can be plotted on a graph used to calculate experimental mass values.

Hydrolysis: 10 ml of sample biodiesel and 1 g of KOH catalyst was placed in 60 ml of methanol and refluxed for 24 hours.[14] After 24 hours, sample was neutralized with a controlled pH acidification procedure.[15] Methanol was recovered and salt was removed from sample.

UV/Vis determination of Free Glycerin: Aqueous stock solutions of acetic acid (1.6 M) and ammonium acetate (4.0 M) were prepared: 195 mg of acetylacetone was added to 5 ml of each solution; 21 mg of sodium metaperiodate was dissolved in 5 ml of acetic acid solution and added to 5 ml of ammonium acetate solution. A working solution of ethanol and water (1:1 v:v) was used to dilute sample volumes to 2 ml. Standard stock was prepared from a 0.03 mg/ml glycerin solution. Standards containing 0, 0.25, 0.50, 0.75, 1.0, 1.25 ml of glycerin stock solution were diluted to 2 ml with working solution. Once volumes were prepared, 1.2 ml of sodium periodate solution was added and samples were stirred for 30 sec. 1.2 ml of acetylacetone was added and placed in a 70° C. water bath and stirred for 1 min. Samples were then read using double beam UV/Vis at 410 nm. Beers law was used to calculate concentrations.[11]

Figure 3:
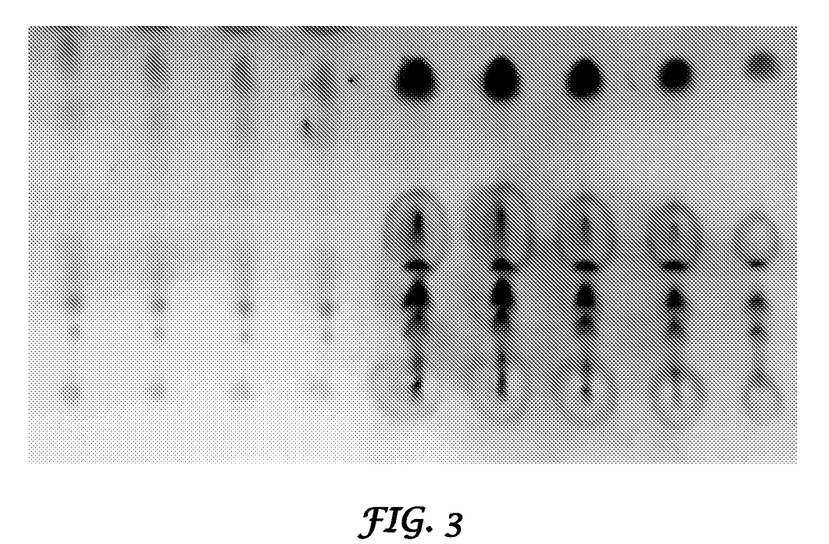
FIG. 3 shows a TLC plate showing calibration on the right and sample on the left.

Two sources of commercially available biodiesel obtained from two different producers were compared by the method described above. The image of the TLC plate is shown in FIG. 3 and the results are shown in Table 1 indicate that this method has a low standard deviation. From the study it can be verified that the testing method used in the present invention is a valid comparison for present GC methods. The results were compared to the ASTM D6584 method (Table 2). ASTM GC testing was done from a commercial lab to compare results independently and to ensure authenticity in validation.

TABLE 1

Results of the TLC studies down on two sources of commercially available biodiesel from two different producers using the Nile Red dye of the present invention.

| Plate A | Mono | Di | Tri |
|---|---|---|---|
|  | 1.85 | 0.61 | 0.31 |
|  | 1.79 | 0.54 | 0.31 |
|  | 1.76 | 0.64 | 0.34 |
|  | 2.22 | 0.53 | 0.29 |
|  | 2.15 | 0.38 | 0.74 |
|  | 2.26 | 0.41 | 0.72 |
|  | 2.14 | 0.40 | 0.58 |
|  | 2.25 | 0.38 | 0.53 |
|  |  | 0.38 |  |
|  |  | 0.51 |  |
| Average mass (µg) | 2.05 | 0.48 | 0.48 |
| STD | 0.21 | 0.10 | 0.19 |

To determine the actual glycerin content in a sample of commercial soy biodiesel, bound glycerides were converted into free glycerol via transesterification, which was then detected using the UV method described by Bondoli et al.[11] This method was preferred because of its ease and because relatively low risk of introducing error with the GC determinations; and because of the nature of the column that makes it unsuitable for high levels of glycerol. Table 3 shows recovery of glycerol which was present in a sample of biodiesel tested using ASTM D6854 methodology.

TABLE 2

Results from commercial source showing ASTM testing results compared to TLC.

| Glyceride species | TLC mass % | Glyceride equivalent multiplier factor | Glyceride equivalent | ASTM D6585 GC mass % | GC glyceride equivalent |
|---|---|---|---|---|---|
| Mono | 6.84 | 0.26 | 1.77 | 0.70 | 0.18 |
| Di | 1.60 | 0.15 | 0.24 | 0.13 | 0.02 |
| Tri | 1.60 | 0.10 | 0.17 | 0.02 | 0.00 |
| Total bound glyceride |  |  | 2.18 |  | 0.20 |

TLC analysis was then compared again directly to the ASTM D6584 determination of free and bound glycerides. A comparison between GC and TLC monoglyceride and diglyceride detection is outlined in Table 4. The difference can have much to do with the fact that the TLC methodology can separate these two classes molecules easily while the GC detection requires the integration of peaks consisting individual molecules. For example, to quantify monoglycerides, there are five peaks which are integrated between the retention times of monoolein and monopalmite. The GC has no discretion where as if TLC methodology is employed; it is simple for anyone to visually verify individual compounds by classes. Quantification becomes less obscure and therefore less deceptive.

Total free glycerol after hydrolysis was performed on a sample of commercial soy obtained in the Midwest (see Table 3). Theoretical yield is calculated from GC results shown in FIG. 4 and using the density of the biodiesel (0.838 g/ml) to obtain the mass percent of glycerol present.

TABLE 3

Total free glycerol after hydrolysis.

| Biodiesel sample | Glycerol |
|---|---|
| a | 1.72 |
| a | 1.71 |
| b | 1.83 |
| b | 1.79 |
| c | 1.72 |
| c | 1.35 |
| Avg. | 1.69 |
| STD | 0.17 |
| RSD | 0.18 |
| Theor. Mass (mg) | 0.79515 |
| Yield | 212.50% |

TLC analysis was then compared again directly to the ASTM D6584 determination of free and bound glycerides. A comparison between GC and TLC monoglyceride and diglyceride detection is outlined in Table 4. The difference can have much to do with the fact that the TLC methodology can separate these two classes molecules easily while the GC detection requires the integration of peaks consisting individual molecules. For example, to quantify monoglycerides, there are five peaks which are integrated between the retention times of monoolein and monopalmite. The GC has no discretion where as if TLC methodology is employed; it is simple for anyone to visually verify individual compounds by classes. Quantification becomes less obscure and therefore less deceptive.

Figure 4:
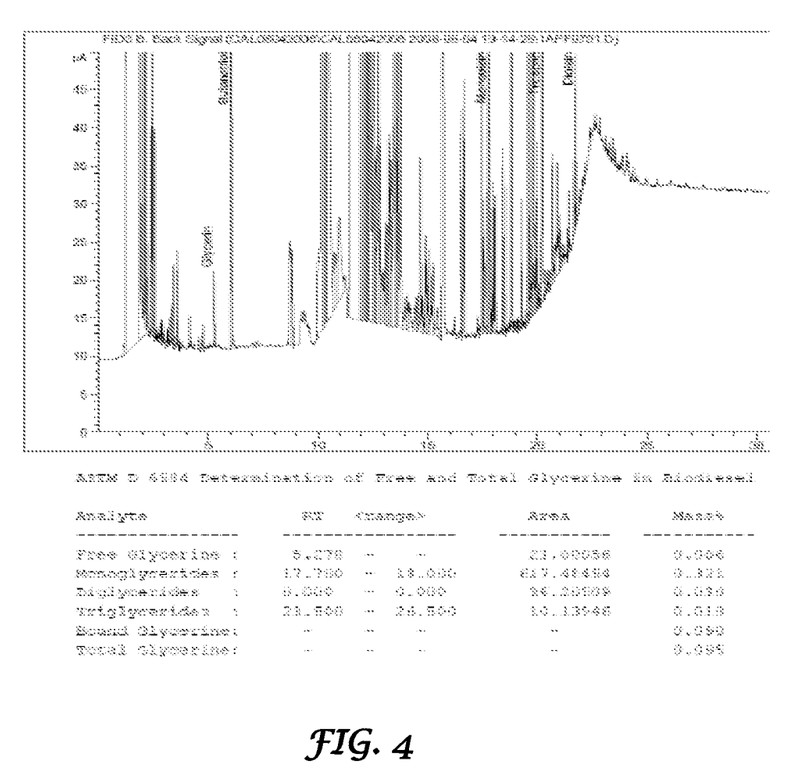
FIG. 4 shows the GC ASTM D6584 results for commercial soy.

In FIG. 4, the actual ASTM GC chromatogram appears to have peaks on top of one another and makes integration very difficult. It is well known that the possibility of absolute detection a class of glyceride by GC is possible only by purchasing standards of all the species or molecules contained in each class. For example in the class of monoglycerides, consists of monoolein, monooleate and monopalmite. This methodology is shown to have a consistent accuracy with approximately ten times the ability of the GC to detect bound glycerides.

Triglycerides were difficult to identify because of overlapping hydrocarbons so only mono and diglycerides are included in the TLC quantification (Table 5).

TLC methodology encounters hardly any limitations present in GC analysis. Water destroys MSTFA and it has been documented that methyl soyate can absorb 1500 ppm of water which is 40 times that of diesel.[16] This offers a possible explanation to the difference in numbers between TLC methodology and GC methodology. Sample preparation is not only easy it is also economical. The present invention demonstrates the means to an end for a fast, cheap, and easy reliable method for the analysis of methyl ester purity.

TABLE 4

Mass percent obtained for monoglycerides and diglycerides present in commercial soy from Midwest.
volume 2 * 0.1 μl

| glycerides | | | mono | | | di |
|---|---|---|---|---|---|---|
| $R^2$ | 1 | | 4.76 | $R^2$ | 0.999 | 6.21 |
| | | | 4.55 | | | 6.65 |
| | | | 4.15 | | | 6.90 |
| | | | 4.95 | | | 7.27 |
| | | | 4.74 | | | 5.66 |
| | STD | | 0.30 | STD | | 0.62 |
| | Avg. (μg) | | 4.63 | Avg. (μg) | | 6.54 |
| | RSD | | 6.57 | RSD | | 9.56 |
| TLC mass % | | | 2.63 | | | 3.71 |
| GC mass % | | | 0.33 | | | 0.03 |

TABLE 5

Total glycerol detection: Comparison between GC methodology and TLC methodology results.

| Mono and Diglycerides TLC | Bound Total GC |
|---|---|
| 1.23 | 0.089 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. US Patent Publication No. 20060213554: Method and apparatus for analysis of relative levels of biodiesel in fuels by near-infrared spectroscopy.
2. CN 101290308: Method for analyzing ferulaic acid butyric glyceride by high performance liquid chromatography.

3. U.S. Pat. No. 4,259,440: Hydrolysis and assay of triglycerides.
4. Lotero, E., Liu, Y., Lopez, D., Suwannakarn, K., Bruce, D., Goodwin, J Jr., J. Ind. Eng Chem. Res., 2005, 44, 5353-5363.
5. Freedman et al., Transesterification Kinetics of Soybean Oil. JAOCS. Vol. 63, no. 10, October 1986.
6. Knothe, G., Analyzing biodiesel: Standards and other methods, JAOCS. Vol. 82, no. 10 (2006).
7. Heiden, 1996
8. Alleman, T. L., McCormick, R. L., Deutch. 2006 B100 Quality Survey Results: Milestone Report. NRE1/TP-540-41549. May 2007.
9. Plank, C., E. Lorbeer, Simultaneous Determination of Glycerol, and Mono-, Di-, and Triglycerides in Vegetable Oil Methyl Esters by Capillary Gas Chromatography, J. Chromatogr. A. 697:461-468 (1995).
10. Plank, C., E. Lorbeer, Quality Control of Vegetable Oil Methyl Esters Used as Diesel Fuel Substitutes: Quantitative Determination of Mono-, Di-, and Triglycerides by Capillary GC. J. High Resolut. Chromatogr. 16:609-612 (1992).
11. Bondioli, P., L. Della Bella, An Alternative Spectrophotometric Method for the Determination of Free Glycerol in Biodiesel, Eur. J. Lipid Sci. Technol. 107:153-157 (2005).
12. Greenspan, P., E. P. Mayer, and S. D. Fowler. Nile red: a selective fluorescent stain for intracellular lipid droplets. J Cell Biol. 100: 965-973 (1985).
13. Fowler, S. D., et. al. Use of nile red for the rapid in situ quantitation of lipids on thin-layer chromatograms. Journal of Lipid Research. 28:1225-1232 (1987).
14. Rashid, V., et. al. Production of Biodiesel Through Optimized Alkaline-Catalyzed Transesterification of Rapeseed Oil. Fuel 87:265-273 (2008).
15. Akgun, N., et. al. Effects of Process Varibles for Biodiesel Production by Tranesterification. Eur. J. Lipids Sci. Technology. 109:486-492 (2007).
16. Lozano, P., N. Chirat, J. Graille and D. Pioch, Measurement of Free Glycerol in Biofuels, Ibid. 354:319-322 (1996). Monos and Di's Boundtotal TLC GC 1.23 0.089

What is claimed is:

1. A thin-layer chromatography (TLC) method for detecting an amount of one or more suspected bound glyceride contaminants in a fuel sample wherein the bound glyceride contaminants comprise monoglycerides, diglycerides and triglycerides using a fluorescent lipophilic dye comprising the steps of:
    obtaining the fuel sample;
    separating the fuel sample along with a standard sample of the suspected contaminants on one or more coated TLC plates;
    submerging the TLC plates in a hydrophobic nonaqueous solution comprising the fluorescent lipophilic dye to stain the plates;
    drying the stained plates;
    dipping the dried plates in a bleach solution;
    visualizing one or more bands on the one or more coated TLC plates using an UV lamp; and
    determining the amounts of the one or more suspected bound glyceride contaminants by comparing a region of interest in the one or more bands on the one or more coated TLC plates for the standard and the fuel sample.

2. The method of claim 1, further comprising the steps of:
    capturing one or more images from the one or more bands on the one or more coated TLC plates after all of the steps in the method of claim 1 have been performed;
    validating an accuracy of the standard sample using a mass curve of known masses versus fluorescent intensity;
    plotting a graph to calculate a R2 value for each plate; and
    calculating one or more masses for the one or more suspected bound glyceride contaminants in the sample by using the mass curve and a measured fluorescent intensity of the one or more suspected bound glyceride contaminants in the one or more bands on the one or more coated TLC plates.

3. The method of claim 2, wherein the one or more calculated masses for the one or more suspected bound glyceride contaminants is directly correlated with an overall composition and purity of the sample.

4. The method of claim 2, wherein the one or more calculated masses for the one or more suspected bound glyceride contaminants is directly correlated with an overall conversion rate of a chemical reaction.

5. The method of claim 4, wherein the chemical reaction is a transesterification reaction.

6. The method of claim 1, wherein the fuel sample is selected from the group consisting of one or more renewable fuels, biofuels, biodiesel, vegetable oils, alkyl esters, and ethanol.

7. The method of claim 1, wherein the fuel sample is deposited on the one or more coated TLC plates directly or deposited on the one or more coated TLC plates after dissolution in an organic liquid.

8. The method of claim 1, wherein the standard sample is deposited on the one or more coated TLC plates directly or deposited on the one or more coated TLC plates after dissolution in an organic liquid.

9. The method of claim 1, wherein one or more coated plates are selected from the group consisting of glass, plastic, aluminum or aluminum foil.

10. The method of claim 1, wherein the one or more coated plates comprise a coating selected from the group consisting of silica gel, aluminum oxide, cellulose or any other adsorbent material.

11. The method of claim 1, further comprising the step of:
    placing the one or more coated TLC plates in a solvent or a solvent mixture for a specified amount of time before submerging the one or more coated TLC plates in the solution of fluorescent lipophilic dye wherein the solvent or solvent mixture comprises, hexane, diethyl ether, acetic acid, organic solvents or any combinations or mixtures thereof.

12. The method of claim 1, wherein the dye solution comprises one or more lipophilic dyes selected from the group consisting of Nile Red, Oil-Red-O, Sudan Black B or other lipophilic stains.

13. The method of claim 1, wherein the one or more coated plates are submerged in a solution of the lipophilic dye until stained.

14. The method of claim 1, wherein the bleach solution is selected from the group consisting of sodium hypochlorite, hydrogen peroxide, sodium perborate, sodium percarbonate, sodium persulfate, sodium perphosphate or calcium hypochlorite.

15. An analytical method for detecting the amounts of one or more suspected bound glyceride contaminants in a fuel sample wherein the bound glyceride contaminants comprise monoglycerides, diglycerides and triglycerides using a fluorescent lipophilic dye comprising the steps of:
    obtaining the fuel sample
    depositing the fuel sample onto a coated plate;
    depositing a standard of the one or more suspected contaminants onto the coated plate;

placing the coated plate in a hydrophobic nonaqueous solvent or a hydrophobic nonaqueous solvent mixture for a specified amount of time;

removing the coated plate from the hydrophobic nonaqueous solvent or the hydrophobic nonaqueous solvent mixture;

drying the coated plate;

submerging the dried coated plate in a hydrophobic nonaqueous fluorescent lipophilic dye solution comprising a fluorescent lipophilic dye;

removing the coated plate from the fluorescent lipophilic dye solution;

drying the coated plate;

dipping the dried coated plate in a bleach solution;

drying the coated plate;

visualizing one or more bands on the coated plate using an UV lamp; and determining the amounts of one or more suspected bound glyceride contaminants by comparing a region of interest in the one or more bands on the coated plate for the standard and the fuel sample.

16. An analytical method for detecting the amounts of one or more suspected bound glyceride contaminants in a biodiesel sample wherein the bound glyceride contaminants comprise monoglycerides, diglycerides and triglycerides using a lipophilic fluorescent dye comprising the steps of:

obtaining the biodiesel sample;

depositing the biodiesel sample onto a coated plate, wherein the biodiesel sample is deposited directly or deposited after dissolution in an organic liquid;

depositing a standard of the one or more suspected bound glyceride contaminants onto the coated plate, wherein the standard is deposited directly or deposited after dissolution in an organic liquid;

placing the coated plate in a hydrophobic nonaqueous solvent or a hydrophobic nonaqueous solvent mixture for a specified amount of time;

removing the coated plate from the hydrophobic nonaqueous solvent or the hydrophobic nonaqueous solvent mixture;

drying the coated plate;

submerging the dried coated plate in a solution of the fluorescent lipophilic dye until stained;

removing the coated plate from the dye solution;

drying the coated plate;

dipping the dried coated plate in a bleaching solution;

drying the coated plate;

visualizing one or more bands on the coated plate using an UV lamp; and determining the amounts of one or more suspected bound glyceride contaminants by comparing a region of interest in the one or more bands on the coated plate for the standard and the biodiesel sample.

17. The method of claim 16, further comprising the steps of:

capturing one or more images from the one or more bands on the coated plate after all of the steps in the method of claim 16 have been performed;

validating an accuracy of the standard using a mass curve of known masses versus fluorescent intensity;

plotting a graph to calculate a R2 value for the plate; and calculating one or more masses for the one or more suspected bound glyceride contaminants in the biodiesel sample by using the mass curve and a measured fluorescent intensity of the one or more suspected bound glyceride contaminants in the one or more bands on the coated plate.

18. The method of claim 17, wherein the one or more calculated masses for the one or more suspected bound glyceride contaminants is directly correlated with an overall conversion rate of a transesterification reaction for the biodiesel sample.

19. The method of claim 16, wherein the dye solution comprises one or more lipophilic dyes selected from the group consisting of Nile Red, Oil-Red-O, Sudan Black B or other lipophilic stains.

* * * * *